(12) United States Patent
LaVean

(10) Patent No.: US 6,230,709 B1
(45) Date of Patent: May 15, 2001

(54) CERVICAL CAP WITH HANGING LOOP FOR REMOVAL

(76) Inventor: Michael G. LaVean, 108 Mill St. Box 31, Saranac, MI (US) 48881

( * ) Notice: Subject to any disclaimer, the term of this patent is extended or adjusted under 35 U.S.C. 154(b) by 0 days.

(21) Appl. No.: 09/595,874

(22) Filed: Jun. 16, 2000

Related U.S. Application Data

(63) Continuation of application No. PCT/US98/01125, filed on Jan. 15, 1998.

(51) Int. Cl.[7] ....................................................... A61F 6/06

(52) U.S. Cl. ........................................... 128/834; 128/837

(58) Field of Search ..................................... 128/830–841

(56) References Cited

U.S. PATENT DOCUMENTS

| | | | | |
|---|---|---|---|---|
| 2,818,064 | * | 12/1957 | Leff ....................................... | 128/841 |
| 4,785,804 | * | 11/1988 | Tlapek ................................. | 128/841 |
| 4,895,170 | * | 1/1990 | Tlapek ................................. | 128/841 |
| 6,155,259 | * | 12/2000 | Conte ................................... | 128/833 |

* cited by examiner

*Primary Examiner*—Michael A. Brown

(57) ABSTRACT

An improved cervical cap positioned over a cervix to concentrate sperm and effect fertilization having a thin-walled, flexible, and pliant dome with an integrally-molded flexible annular rim. The cervical cap further includes an elongated string of elastomeric material having first and second ends. The first end of the elongated string is connected to the apex portion of the dome and the second end is connected to a loop for removing the cap from a vaginal cavity. The loop is intended to remain outside the vaginal cavity when the cap is positioned over the cervix.

19 Claims, 1 Drawing Sheet

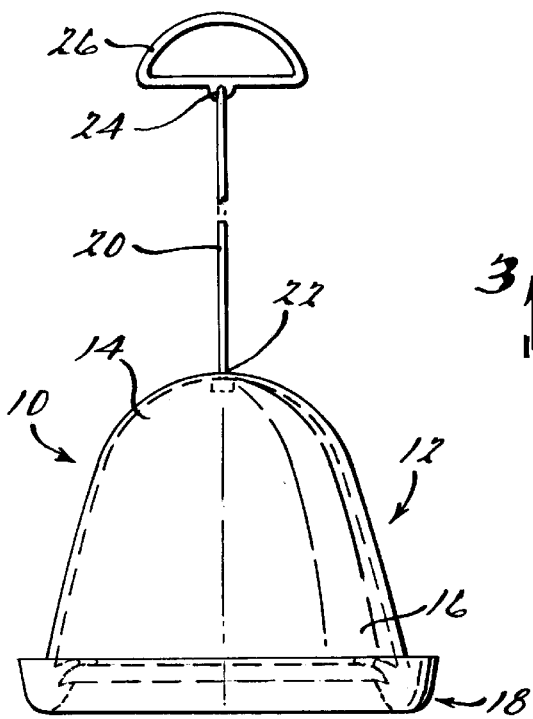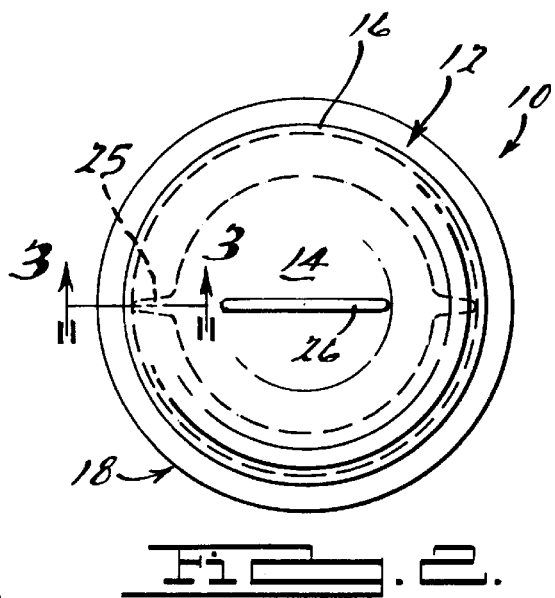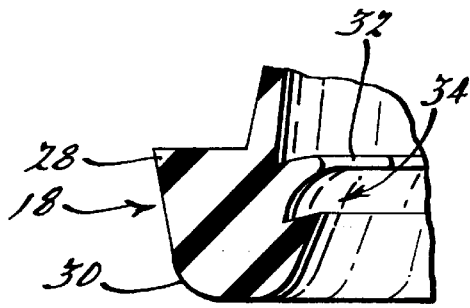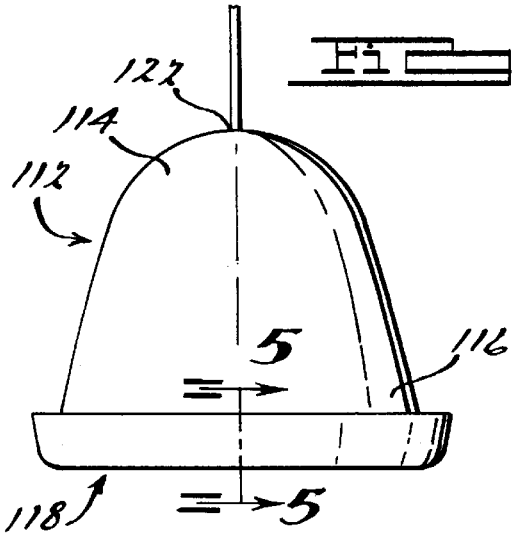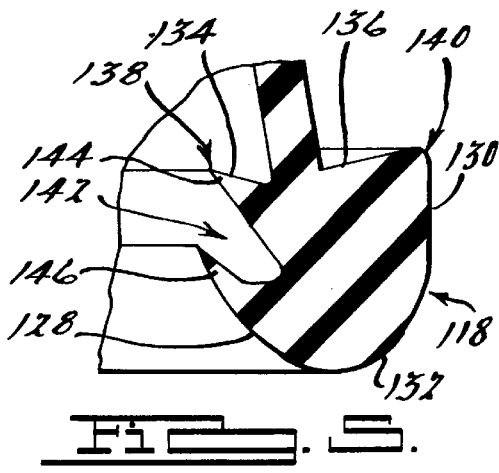

CERVICAL CAP WITH HANGING LOOP FOR REMOVAL

This application is a continuation of PCT/US98/01125, filed Jan. 15, 1998.

BACKGROUND OF THE INVENTION

1. Field of the Invention

The present invention relates generally to conception devices for females and, more particularly, to an improved cervical cap with a hanging loop for removal.

2. Discussion of the Related Art

Devices which are intended to be inserted into the vagina are known for use as contraceptive barriers. One particular contraceptive device, the cervical cap, is placed over the cervix to prevent semen from entering the cervical canal and is held in place according to a suction grip by precise fit or by a formassuming dome using the surface viscosity of a moist cervical surface. Some of these previous cervical caps are made of latex. However, because latex may cause sperm damage, possibly resulting in deformed abnormal children, the latex cap should not be used for delivery of sperm. In addition, all of these devices are geared only towards the prevention of pregnancy.

Currently, however, there are parts of the population that are experiencing a decline in fertility and would benefit from an invention that increases the likelihood of conception. Some of the primary factors contributing to a decline in fertility are low sperm counts, problems with the sperm motility, and a hostile vaginal environment due to infection or other chronic conditions. A method used to overcome these problems is sperm concentration at the cervical Os, which is the area connecting the uterus and the vaginal cavity. Sperm concentration significantly increases the probability of conception, as fewer sperm are needed to effect fertilization since a higher number reach the uterus in tact. Since these sperm travel a shorter distance, a higher proportion remain viable upon reaching the uterus. In cases of low sperm counts or poor motility, this is particularly effective. In addition, a potentially hostile and vaginal environment is bypassed.

Methods in use today to address fertility issues are administered only by medical professionals and are very costly. As an example, administration of sperm using a pipet that is inserted through the Os damages fragile cervical tissue and can cause extensive bleeding. In addition, the medical procedure is painful and involves considerable investments of time and money.

Additionally, there exists cultural bias in some areas of the world, particularly in Middle Eastern cultures, toward digital insertion. These cultures feel that medical interventions and physical manipulations by doctors are contradictory to their beliefs.

Thus, a significant portion of the female population would benefit from being able to manually insert and remove a cervical cap, thus reducing the number of doctor visits and intervention by medical personnel and increasing the comfort of the patient. There is a need, therefore, for an inexpensive cervical cap that may be inserted by a woman and remain in place for an extended period of time to effect fertilization.

The present invention provides an improved cervical cap which overcomes the aforementioned problems. Due to its novel construction, the cervical cap of the present invention allows for the easy removal of the cervical cap by a woman upon completion of fertilization.

SUMMARY OF THE INVENTION

The present invention relates to a cervical cap which is positioned over a female's cervix to increase the chances of successful fertilization and allow for easy removal by the female. The present invention provides a cervical cap having a thin-walled, flexible, and pliant dome with an integrally-molded flexible retaining rim. In position, the flexible, form-assuming dome of the cervical cap conforms to the exocervical surface to closely fit the surface upon contact. Due to its thinness and applicability, the dome of the cap will continue to adhere to the surface of the cervix until removed. Adherence of the dome to the cervix is further facilitated by the moist cervical surface.

The improved cervical cap of the present invention further includes an elongated string of elastomeric material attached at the apex of the dome portion of the cap and culminating in a loop for easy removal of the cap. Thus, while the cap is in place over the cervix, the loop hangs outside of the vaginal cavity by way of the elongated string, thereby making it possible to remove the cap without making an insertion into the vaginal cavity.

Additional advantages and features of the present invention will become apparent from the subsequent description in the appended claims, taken in conjunction with the accompanying drawings.

BRIEF DESCRIPTION OF THE DRAWINGS

FIG. 1 is a side view of a preferred embodiment of a cervical cap of the present invention;

FIG. 2 is a top elevational view of the cervical cap;

FIG. 3 is a sectional view, taken along line 3—3 in FIG. 2;

FIG. 4 is a side view of an alternate preferred embodiment cervical cap of the present invention; and FIG. 5 is a sectional view, taken along line 5—5 in FIG. 4.

DETAILED DESCRIPTION OF THE PREFERRED EMBODIMENT

Referring to FIG. 1, a preferred embodiment of a cervical cap with an elongated string of elastomeric material of the present invention is illustrated and indicated generally by the numeral 10.

Generally speaking, cervical cap 10 comprises a flexible, thin, form-assuming dome 12, an apex portion 14, a base portion 16, and an annular rim 18. Dome 12 is generally thimble-shaped, with base portion 16 inwardly tapering toward apex portion 14. The outer diameter of rim 18 is greater than that of base portion 16 of dome 12.

Cervical cap 10 further includes an elongated string of elastomeric material 20. Elongated string 20 includes a first end 22 and a second end 24, where first end 22 is connected to apex portion 14 and second end 24 is connected to a loop 26. The first and second ends may be molded to the apex portion and loop, respectively, or alternatively, attached as separate components. Loop 26 is intended to remain outside the vaginal cavity when cap 10 is positioned over the cervix.

In a preferred embodiment, referring particularly to FIGS. 2 and 3, annular rim 18 has an inner surface 28 and an outer surface 30. Thin, gripping finger 32 projects radially inwardly, as finger 32 is integrally-formed with inner surface 28. Finger 32 also defines an upper portion of a notched indentation 34 as viewed in FIG. 3. Annular rim 18 contains at least two gripping fingers 32 that are directly opposite or symmetrically opposed from each other along inner surface 28. However, it will be appreciated to one skilled in the art that more than two fingers could be employed.

Each finger 32 has at least one notch 25 to permit the finger to bend towards crown section 14 of dome 12 during insertion of the cap. Fingers 32 effectively grip and hold cervical cap 10 over the cervix in order to prevent semen from entering the cervical canal. Gripping fingers 32 and notches 25 essentially provide the effect of a Chinese finger puzzle by gripping the side walls of the cervix and holding the cap when the circumference of the rim 18 is fitted around the cervix and slightly expands. Cervical cap 10 is fixed in place by the use of gripping fingers 32 rather than merely by suction or surface viscosity.

Referring now to FIGS. 4 and 5, an alternate embodiment of the present invention provides a cervical cap 110 comprising a flexible, thin, form-assuming dome 112, an apex portion 114, a base portion 116, and an annular rim 118. Dome 112 is generally thimble-shaped, with base portion 116 inwardly tapering toward apex portion 114. The outer diameter of rim 118 is greater than that of base portion 116 of dome 112.

Cervical cap 110 further includes an elongated string of elastomeric material 120. Elongated string 120 includes a first end 122 and a second end 124, where first end 122 is connected to apex portion 114 and second end 124 is connected to a loop 126. Loop 126 is intended to remain outside the vaginal cavity when cap 110 is positioned over the cervix.

Referring particularly to FIG. 5, rim 118 has an inner surface 128 and an outer surface 130, bottom surface 132, and upper surfaces 134 and 136. Upper surface 134 extends leftward from base portion 116, as viewed in FIG. 5, and terminates at outer shoulder 138. Upper surface 136 extends rightward from base portion 116, as viewed in FIG. 5, and terminates at outer shoulder 140. Upper surface 136 extends at an acute angle from adjacent base portion 116, preferably, for example, at about an 85 degree angle.

Annular rim 118 has generally inwardly directed annular groove 142. The side walls or annular groove 142 extend generally toward bottom surface 132 with the opening of annular groove 142 facing inwardly and upwardly as shown in FIG. 5. Adjacent to annular groove 142 are annular upper rim 144 and annular lower rim lip 146. As illustrated in FIG. 5, both upper rim lip 144 and lower rim lip 146 extend generally inwardly and upwardly at an angle acute to dome base portion 116. This lip configuration serves to grip the cervix wall and helps keep the cervical cap in position over the cervix as an alternate embodiment to the configuration shown in FIGS. 2 and 3.

It is preferred that the cervical cap of the present invention be constructed of a sperm-impermeable, tear-resistant medical elastomer, such as a silicone rubber, and formed by liquid injection molding. Other suitable materials, such as RTV thermoplastic that can be molded thin enough to be form-conforming and pliant may also be employed. The elongated string is preferably made of the same elastomeric material as the cap, such as silicone rubber.

Preferred materials include a 40 durometer silicone, such as Silastic Q4840 (Dow Corning) or Silicone 4040 (Bayer). When thinly molded, these materials allow for up to a 600% stretch of the molded product.

The elongated string is preferably made of the same elastomeric material as the cap, such as silicone rubber.

This material may or may not be impregnated with biologically active components. These components may include, but are not limited to, spermicides, antibiotics, antifungals, and hormonal replacements. The biologically active components would assist in fertilization, or may be mixed with sperm within the hollow body of the dome of the cap in order to achieve the desired result. The use of biologically active materials may stimulate sperm motility, prolong the active life of the sperm or aid in gender selection. Selectively eliminating or altering the behavior of some sperm by significantly changing the pH may bias the activity of the X or Y sperm, resulting in odds which favor one particular sex over the other. These components may be released therefrom in an amount effective to achieve its purpose during use.

Although the description as set forth is in conjunction with human subjects, it will be further appreciated that the claimed products may be readily adaptable for use with animal subjects having a cervix.

While it will be apparent that the preferred embodiments disclosed are well calculated to provide the advantages and features above stated, it will be appreciated that the invention is susceptible to modification, variation, and change without departing from the proper scope or fair meaning of the subjoined claims.

What is claimed is:

1. An improved cervical cap positioned over a cervix to concentrate sperm and effect fertilization comprising:
   (a) a thin, form-assuming flexible dome having a hollow body and an interior and exterior surface, said dome comprising an apex portion and a base portion,
   (b) a flexible, annular rim integrally-molded with said base portion and having an inner and outer surface,
   (c) an elongated string of elastomeric material having first and second ends, said first end of said elongated string connected to said apex portion of said dome and said second end connected to a loop for removing said cap from a vaginal cavity;
   wherein said loop remains outside said vaginal cavity when said cap is positioned over said cervix.

2. The cervical cap of claim 1, wherein said cap further comprises at least two thin, gripping fingers projecting radially inwardly, said fingers being integrally-formed with said inner surface of said rim, and at least two circumferentially spaced apart notches disposed between said fingers to permit said fingers to bend towards said crown section of said dome during insertion of said cap and to effectively grip and hold said cap over said cervix.

3. The cervical cap of claim 1, wherein said annular rim further comprises an inner and outer surface and a bottom surface, said inner surface having an annular groove descending acutely from an inner wall toward said bottom surface of said rim, whereby said annular groove defines an ascending lip on said inner surface of said rim.

4. The cervical cap of claim 3, wherein said rim includes an outer shoulder beveled with respect to said exterior surface of said dome.

5. The cervical cap of claim 1, wherein said cap is comprised of a sperm-impermeable medical elastomer.

6. The cervical cap of claim 1, wherein said cap is comprised of silicone rubber.

7. The cervical cap of claim 1, wherein said cap further comprises sperm within said body of said dome.

8. The cervical cap of claim 1, wherein said cap is comprised of a biologically active material.

9. The cervical cap of claim 1, wherein a biologically active material is mixed with sperm within said hollow body of said dome.

10. The cervical cap of claim 1, wherein said cap is of a size suitable for use with a human.

11. The cervical cap of claim 1, wherein said cap is of a size suitable for use with an animal.

12. An improved cervical cap positioned over a cervix to concentrate sperm and effect fertilization comprising:
   (a) a thin, form-assuming flexible dome having a hollow body and an interior and exterior surface, said dome comprising an apex portion and a base portion;
   (b) a flexible, annular rim integrally-molded with said base portion having an inner and outer surface;
   (c) at least two thin, gripping fingers projecting radially inwardly, said fingers being integrally-formed with said inner surface of said rim, and at least two circumferentially spaced apart notches disposed between said fingers to permit said fingers to bend towards said crown section of said dome during insertion of said cap and to effectively grip and hold said cap over said cervix; and
   (d) an elongated string of elastomeric material having first and second ends, said first end of said elongated string connected to said apex portion of said dome and said second end connected to a loop for removing said cap from a vaginal cavity;
   wherein said loop remains outside said vaginal cavity when said cap is positioned over said cervix.

13. The cervical cap of claim 12, wherein said cap is comprised of a sperm-impermeable medical elastomer.

14. The cervical cap of claim 12, wherein said cap is comprised of silicone rubber.

15. The cervical cap of claim 12, wherein said cap further comprises sperm within said body of said dome.

16. The cervical cap of claim 12, wherein said cap is comprised of a biologically active material.

17. The cervical cap of claim 12, wherein a biologically active material is mixed with sperm within said hollow body of said dome.

18. The cervical cap of claim 12, wherein said cap is of a size suitable for use with a human.

19. The cervical cap of claim 12, wherein said cap is of a size suitable for use with an animal.

* * * * *